United States Patent [19]
Hilgenfeldt et al.

[11] Patent Number: 5,529,491
[45] Date of Patent: Jun. 25, 1996

[54] AESTHETIC ORTHODONTIC BAND AND WELDED ATTACHMENT ASSEMBLY

[75] Inventors: Thorsten G. Hilgenfeldt, Montrose; Allen B. Amundson, Upland; Nicholine M. Sandoval, Monrovia; Fantu W. Leka, La Verne; Robert C. Manemann, Huntington Beach; Casey A. Campbell, Arcadia, all of Calif.

[73] Assignee: Minnesota Mining and Manufacturing Company, St. Paul, Minn.

[21] Appl. No.: 311,349

[22] Filed: Sep. 23, 1994

[51] Int. Cl.⁶ .................................................. A61C 7/18
[52] U.S. Cl. .............................. 433/23; 433/8; 219/117.1
[58] Field of Search .................... 433/2, 3, 8, 23; 219/117.1

[56] References Cited

U.S. PATENT DOCUMENTS

| | | | |
|---|---|---|---|
| 2,062,395 | 12/1936 | Brusse et al. | 433/23 |
| 2,527,526 | 10/1950 | Brusse | 433/15 |
| 3,657,817 | 1/1972 | Kesling | 433/14 |
| 3,896,286 | 7/1975 | Minors | 219/86.8 |
| 3,905,111 | 9/1975 | Kesling | 433/8 |
| 3,955,282 | 5/1976 | McNall | 433/9 |
| 3,985,282 | 10/1976 | Miller et al. | 228/175 |
| 4,083,113 | 4/1978 | Miller et al. | 433/17 |
| 4,249,060 | 2/1981 | Colby | 433/24 |
| 4,842,513 | 6/1989 | Haarmann | 433/9 |
| 5,123,845 | 6/1992 | Vassiliadis et al. | 433/215 |
| 5,154,606 | 10/1992 | Wildman | 433/8 |
| 5,161,969 | 11/1992 | Pospisil et al. | 433/8 |
| 5,232,364 | 8/1993 | Rosen | 433/173 |
| 5,338,191 | 8/1994 | Hamula | 433/23 |

FOREIGN PATENT DOCUMENTS

256283  10/1988  Japan .................... 219/117.1

*Primary Examiner*—Stephen Funk
*Attorney, Agent, or Firm*—Gary L. Griswold; Walter N. Kirn; James D. Christoff

[57] ABSTRACT

An orthodontic assembly that includes a band and an attachment has one or more spot welds to secure the band to the attachment. The spot welds are characterized by the lack of any outer surface weld deformation that is circular in shape, or that is visible to the naked eye when viewed at a distance of twenty-four inches. Apparatus for welding the attachment to the band includes a subframe that is swingable in an arc to follow the inner contour of the band in order to provide automated welding on mesial and distal sides of the attachment.

8 Claims, 5 Drawing Sheets

AESTHETIC ORTHODONTIC BAND AND WELDED ATTACHMENT ASSEMBLY

BACKGROUND OF THE INVENTION

1. Field of the Invention

This invention relates to a welded orthodontic assembly, and particularly concerns an orthodontic band that is welded to a bracket, buccal tube or other orthodontic attachment.

2. Description of the Related Art

Orthodontic treatment involves movement of the teeth to desired positions. During treatment, small slotted bodies known as brackets are typically affixed to anterior, cuspid and bicuspid teeth, and small devices known as buccal tubes are secured to molar teeth. An arch wire held in slots of the brackets and channels in the buccal tubes functions as a track to guide movement of the teeth to orthodontically correct positions. The teeth are often moved by bends or twists placed in the arch wire or by elastic members connected between the brackets or buccal tubes of certain teeth.

In past years, it was common practice to weld each buccal tube and bracket to a respective orthodontic band. The orthodontic bands were selected to match the contour and circumferential dimension of the tooth, so that a close, non-loosening fit between the band and the tooth could be obtained. In more recent years, however, adhesives have been developed that usually have sufficient strength to securely affix brackets directly to the tooth surfaces.

However, buccal tubes are often subjected to relatively large forces from occluding teeth as well as forces exerted by the arch wire. As such, it is still common practice to weld buccal tubes to an metallic orthodontic band so that a stable base for the buccal tube is provided. Welded bracket and band assemblies are also still used with anterior, cuspid and bicuspid teeth in instances where a relatively strong connection to the tooth is desired.

In addition to brackets and buccal tubes, other orthodontic devices or "attachments" may also be welded to bands. Examples of such other attachments include cleats, buttons, hooks, lingual sheaths and eyelets, and such attachments may be mounted on either the buccolabial side (i.e., facing the cheeks or lips) or the lingual side (i.e., facing the tongue) of the band.

Many types of attachments are provided with welding flanges that extend in mesial and distal directions. The flanges facilitate welding the attachment to the band by providing an additional surface for electrical and physical contact with electrodes of the welder.

Past welding processes for manufacturing orthodontic attachment and band assemblies have included an initial tack welding step wherein the attachment is received in a recess of a fixture. The fixture including the recess is electrically connected to one electrode of the welder and the other electrode is brought into contact with an inner surface of the band. After completion of tack welding to temporarily affix the attachment to the band, the assembly is removed from the tack welder and taken to a finish welder for final welding.

Finish welding is often carried out by placing one electrode of the finish welder in contact with an outer surface of the attachment flanges, while contacting the inner surface of the band adjacent the attachment to the other electrode of the finish welder. The finish weld process has often been carried out by hand. Commonly, the operator grips the tack welded assembly and places the flanges of the attachment and the adjacent area of the band between the electrodes of a higher current, finish spot welder. Oftentimes, four spot welds are provided, two in each of the two flanges.

In the step of finish welding orthodontic attachments to bands, both electrodes typically have identical cylindrical shapes of relatively small diameter. As current flows between the electrodes during the welding process, a weld is obtained at the interface of the band and the attachment along a path that represents the path of least electrical resistance, which is typically the shortest path through the assembly between the ends of the two electrodes. The small diameter of the cylindrical electrodes enables the current to be directed toward a particular area where the weld is desired.

There is a continuing need in the art to improve the aesthetics of orthodontic assemblies. Unfortunately, conventional welded assemblies are often characterized by relatively visible deformations on the surface of the welding flanges, which may detract from the smooth appearance of remaining external surfaces of the assembly. If the deformations are sufficiently large, the deformations may function as a site that retains small food particles or bacteria or function as a site that may initiate corrosion.

In the past, it has also been known to weld a band to a bracket without flanges. In the manufacture of such assemblies, a tack weld was utilized to initially fix the bracket to the band, and a finish weld was later applied such that the substantial majority of any weld deformations appeared on the inside of the band. However, such practice has not been extended to brackets having flanges, because such brackets are wider in a mesiodistal direction and the flanges provide better anchorage locations for the finish welds.

SUMMARY OF THE INVENTION

The present invention is directed toward an orthodontic assembly that comprises a metallic band for encircling a tooth, wherein the band has an inner surface and an outer surface. The assembly also includes a metallic orthodontic attachment that is connected to the band, wherein the attachment has at least one welding flange with an outer surface. The assembly additionally includes at least one spot weld between each flange and the outer surface of the band, and the spot weld(s) interconnect the attachment and the band with a strength sufficient for orthodontic treatment. The outer surface of each welding flange is characterized by a lack of any welding deformation that is circular in shape.

In addition, the present invention is directed toward an orthodontic assembly that comprises a metallic band for encircling a tooth, wherein the band has an inner surface and an outer surface. The assembly also includes a metallic orthodontic attachment that is connected to the band, wherein the attachment has at least one welding flange with an outer surface. The assembly additionally includes at least one spot weld between each flange and the outer surface of the band, and the spot weld(s) interconnect the attachment and the band with a strength sufficient for orthodontic treatment. The outer surface of each welding flange is characterized by a lack of any welding deformation when viewed by the naked eye at a distance of 24 inches.

The present invention is also directed toward a method of welding an orthodontic attachment to a band. The method includes the steps of placing the attachment in a holder, and electrically connecting the attachment to one electrode of an electric resistance spot welder. The band is placed in a fixture in a certain orientation such that an outer surface of the band is directly adjacent an inner surface of the attachment. An electrode is placed in contact with an inner surface of the band, and a current is directed in a first instance along a path extending between the electrodes and through the band and the attachment to provide a first spot weld. The electrode and the band are relatively moved in an arc while retaining the band in the certain orientation relative to the attachment. A current is directed in a second instance along a path extending between the electrodes and through the band and the attachment after the aforementioned step of relatively moving the electrode and the band in order to provide a second spot weld that is spaced from the first spot weld in an arc along the inner surface of the band.

The invention in its various embodiments is advantageous, in that the welded assembly is aesthetic when viewed toward its external surfaces. The deformations are difficult to see and not pronounced as is common with conventional welded assemblies. The lack of sharp deformation edges provides comfort to the patient. Moreover, the step of tack welding the attachment to the band as was common in prior art practice may be avoided, so that alignment of the attachment to the band and finish welding of the assembly may occur in a one-step operation.

DETAILED DESCRIPTION OF THE PREFERRED EMBODIMENTS

Figure 1:
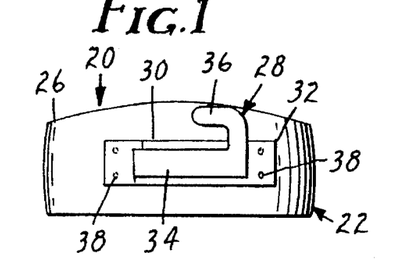
FIG. 1 is a side elevational view looking toward an outer, or buccolabial, surface of an exemplary orthodontic assembly constructed in accordance with the invention.
Figure 3:
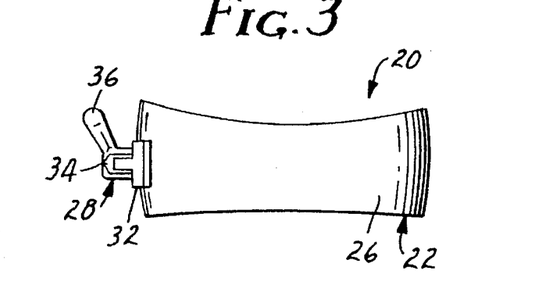
FIG. 3 is an end elevational view looking toward a mesial side of the assembly illustrated in FIGS. 1 and 2.

FIGS. 1 and 3 illustrate for exemplary purposes an orthodontic assembly 20 constructed in accordance with the principles of the present invention. The assembly includes a metallic band 22 for encircling a tooth. The band 22 has a diameter and contour to closely match the diameter and contour of the selected tooth. The band 22 has an inner surface 24 facing the encircled tooth and an outer surface 26 facing away from the tooth.

Figure 2:
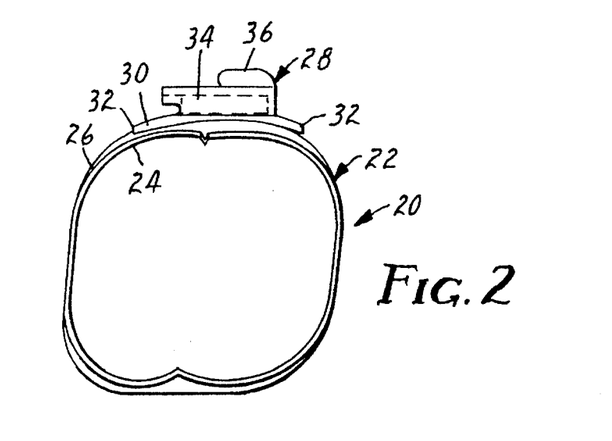
FIG. 2 is a plan view of the assembly illustrated in FIG. 1.

The assembly 20 also includes a metallic orthodontic attachment 28 that, in the example shown in the drawings, is a single passage buccal tube particularly adapted for use with the first molar teeth. The buccal tube attachment 28 includes a base 30 and a pair of welding flanges 32 that extend away from the base 30 in opposite, mesial and distal directions. Each welding flange 32 has an outer or buccolabial surface facing away from the tooth, and an inner or lingual surface that is in contact with the outer surface 26 of the band 22.

The attachment 28 further includes a body 34 surrounding the passage, and also a hook 36. The base 30, the welding flanges 32, the body 34 and the hook 36 are integral and made for example of stainless steel by a metal injection molding process, by a casting process or by a machining process. The passage has a shape adapted to receive an end of an orthodontic arch wire.

The buccal tube attachment 28 shown in FIGS. 1–3 is only one example of a variety of attachments that may be utilized with the assembly of the present invention. Other examples of orthodontic attachments include brackets, cleats, buttons, hooks, eyelets and other devices as may be deemed desirable by the practitioner. Bands for other teeth (such as anterior, cuspid or bicuspid teeth) may also be used in place of the molar band shown in the drawings.

The assembly 20 also includes at least one spot weld interconnecting the attachment 28 to the band 22. In FIG. 1, the numeral 38 illustrates the location of four spot welds that are provided to securely interconnect the welding flanges 32 to the band 22. Each spot weld is located in an area between the inner surfaces of the welding flanges 32 and the outer surface 26 of the band 22, and the welds together join the attachment and the band 22 with a strength sufficient for orthodontic treatment so that the attachment 28 normally does not detach from the band 22 as treatment progresses.

The location of spot welds are often highly visible in conventional welded orthodontic assemblies because of deformation of the metal due to localized high temperatures that are present in the vicinity of the joint as it is welded. The deformations typically result in areas where the electrodes contact the metallic parts, and may be enhanced due to localized arcing that occurred during welding in regions where portions of the electrodes are slightly spaced from adjacent portions of the metal parts. The spot weld itself is typically not visible, as it is located between the parts.

In accordance with the present invention, the outer, exposed surfaces of the welding flanges 32 have only small, if any, deformations, and such deformations are difficult to see under ordinary viewing conditions. The volume of the weld deformation adjacent each spot weld location 38 is greater on the inner surface 24 of the band 22 than the volume of any deformations on the outer surfaces of the welding flanges 32 adjacent the same spot weld location 38.

The volume of the deformations is measured using microprobes that are guided across surfaces adjacent the spot weld locations 38. The microprobes follow the contour of the surfaces, and provide an indication of the volume of the deformation relative to an average height of surfaces surrounding the deformation. Preferably, the microprobes are connected to a programmable X–Y axis robotic arm that is programmed to move the microprobe across the entire area of the deformation as well as adjacent surfaces so that a volume measurement of the deformation can be accurately obtained.

Preferably, no weld deformations are visible on the outer surfaces of the welding flanges when the attachment is viewed at a distance of 24 inches (61 cm) from the naked eye under normal room lighting. More preferably, no deformations are visible on the outer surfaces of the welding flanges when the attachment is viewed at a distance of 12 (30.5 cm) inches from the naked eye under normal room lighting.

An automated welding apparatus 40 for welding the assembly 20 is illustrated in FIGS. 4–9. The apparatus 40 includes a frame 42, an upright hollow housing 44 and a weld head 46 ("Thin-line" brand weld head, from Unitek Equipment). An electrode holder 48 is clamped to a vertically movable shaft of the weld head 46 and has a lower split, depending arm that releasably receives an L-shaped upper electrode 50.

The electrode holder 48 is connected by a conductive strap (not shown) to one terminal of a power supply 52 ("Dual Pulse 125" stored energy resistance welding power supply; from Unitek Equipment). The power supply 52 is shown schematically in FIG. 6. The weld head 46 includes an adjustable pressure sensor electrically connected to the power supply 52 for initiating the flow of current to the upper electrode 50. When the shaft of the weld head 46 descends to a degree sufficient to contact the parts to be welded with sufficient force to exceed a selected, preset pressure, the pressure sensor triggers the power supply to direct one or more pulses of current to the upper electrode 50 to provide a spot weld.

A carriage 54 of the apparatus 40 has two pair of bearing blocks 56 (FIGS. 4 and 5), each pair of which slides on a respective rail 58 that is fixed to the frame 42. A double acting pneumatic piston and cylinder assembly 60 (FIG. 5) is connected to the carriage 54 and the frame 42, and is operable to slide the carriage 54 in a horizontal, front-to-back or "Y" axis direction relative to the frame 42 when desired to either a front or back position.

Solenoid operated air valves (not shown) are interposed in tubing leading to the cylinder of the piston and cylinder assembly 60, and the air valves are electrically connected to a programmable logic controller 62 (series no. SLC-500; Allen Bradley). The controller 62 is shown schematically in FIG. 6 and is electrically connected to the power supply 52. Front and back adjustable micrometer stops 64 (FIG. 5) are connected to the frame 42 for limiting the front and back extent of the path of travel of the carriage 54 relative to the frame 42.

Figure 4:
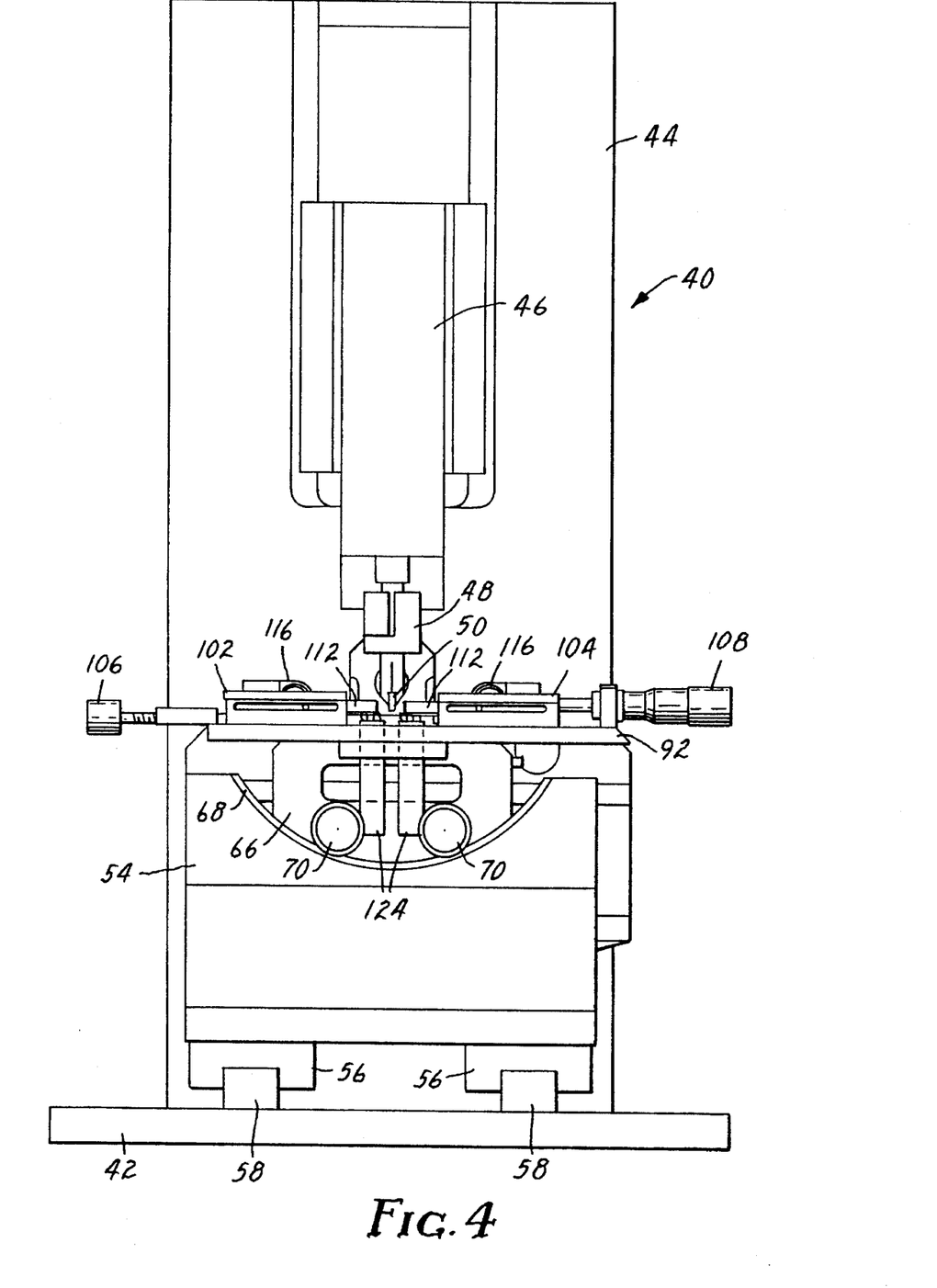
FIG. 4 is a reduced front elevational view of an automated apparatus for manufacture of the assembly shown in FIGS. 1–3.

A subframe 66 is carried by upstanding front and rear arms of the carriage 54. As illustrated in FIG. 4, the front arm of the carriage 54 includes a curved track 68 that has a shape of a partial circle. A pair of rollers 70 that are connected to the subframe 66 travel along a curved path guided by the track 68. An eccentric adjustment 72 (see FIG. 5) interconnects the rollers 70 and the subframe 66 to enable adjustment as may be needed to ensure that each roller 70 bears upon the track 68 with equal pressure.

The rear upstanding arm of the carriage 54 carries a bearing block that receives a shaft 74. The shaft 74 is connected by intermeshed gears (not shown) to a stepmotor 76 (model S83-62-MO microstepping motor/drive system; Compumotor Division, Parker Hannifin Corp.). Activation of the stepmotor 76 by a microstepping drive 77 (FIG. 6) connected to the controller 62 enables the subframe 66 to swing relative to the carriage 54 in a partial arc about a horizontal axis. When the carriage 54 is moved forwardly or rearwardly by the piston and cylinder assembly 60, the downstream gear of the intermeshed gears moves forwardly relative to the upstream gear but remains intermeshed with the latter so that the stepmotor 76 is operable to swing the subframe 66 regardless of whether the carriage 54 is in its rearward or forward position.

Figure 5:
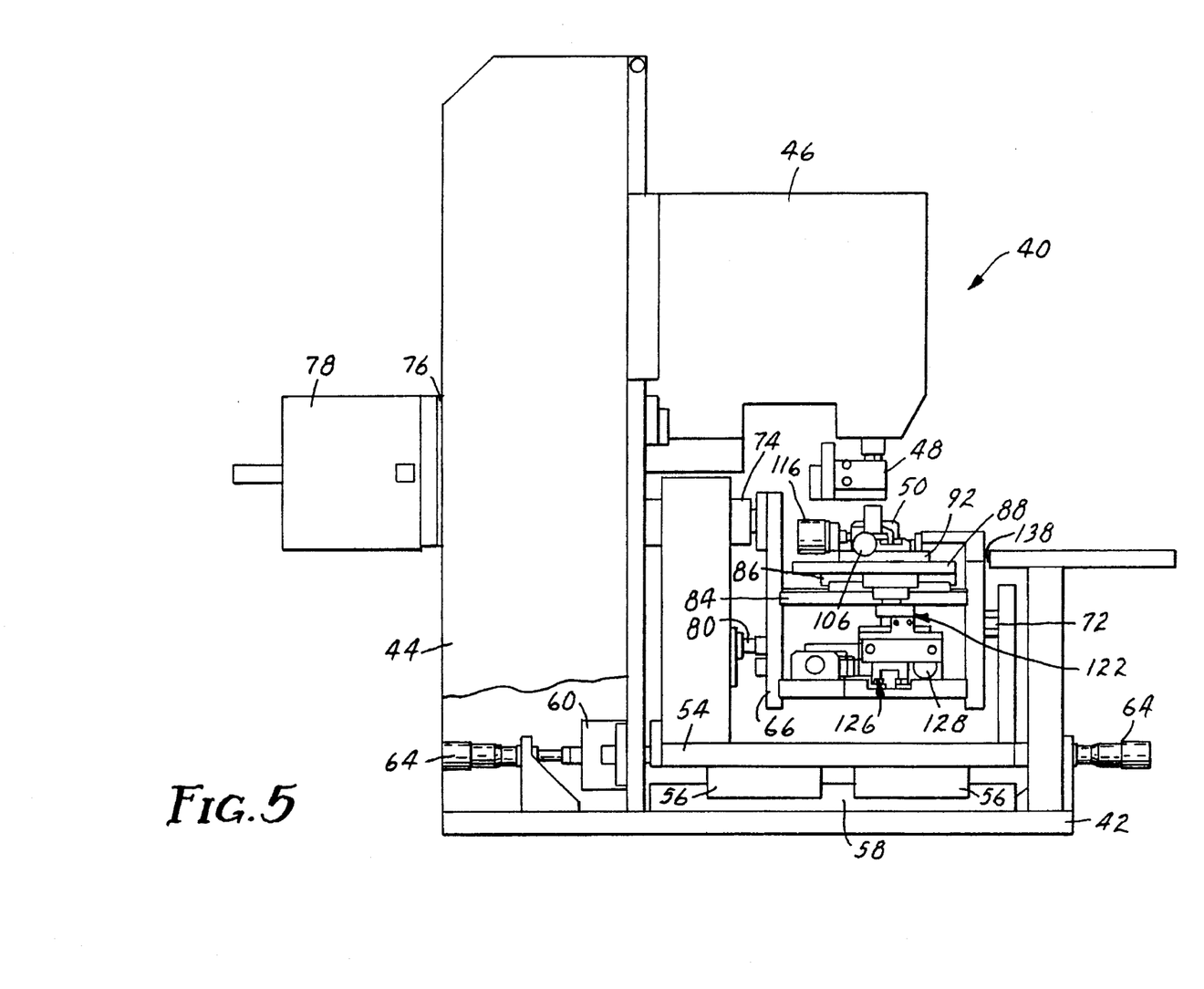
FIG. 5 is a reduced side elevational view of the apparatus depicted in FIG. 4.
Figure 6:
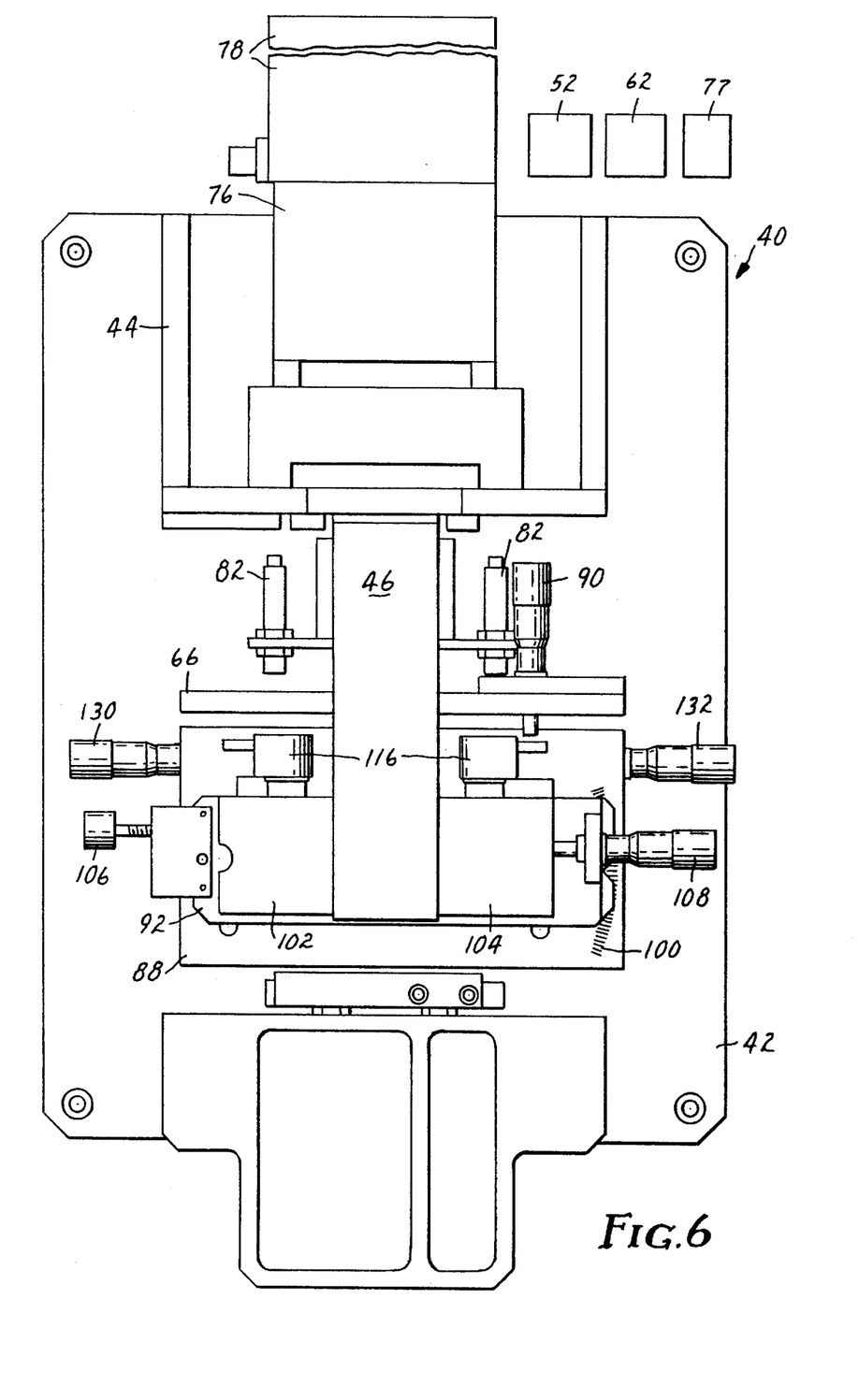
FIG. 6 is an enlarged plan view of the apparatus illustrated in FIGS. 4 and 5.

The stepmotor 76 is shown in FIGS. 5 and 6 and is connected to an encoder 78 (model no. E151000C865; from Dynapar). The encoder 78 is electrically connected to the microstepping drive 77. The encoder 78 provides confirmation of the rotative position of the shaft of the stepmotor 76 and hence of the subframe 66. A photosensor 80 (FIG. 5) is also connected to the microstepping drive 77 and senses the arrival of a projecting member connected to the subframe 66, in order to enable the microstepping drive 77 to determine a "home" position during start-up of the apparatus 40.

As illustrated in FIG. 6, a pair of additional photosensors 82 are provided and are electrically connected to the microstepping drive 77. The photosensors 82 enable the microstepping drive 77 to limit the rocking path of travel of the subframe 66 by sensing the arrival of the same projecting member sensed by the photosensor 80 to determine the home position.

Figure 7:
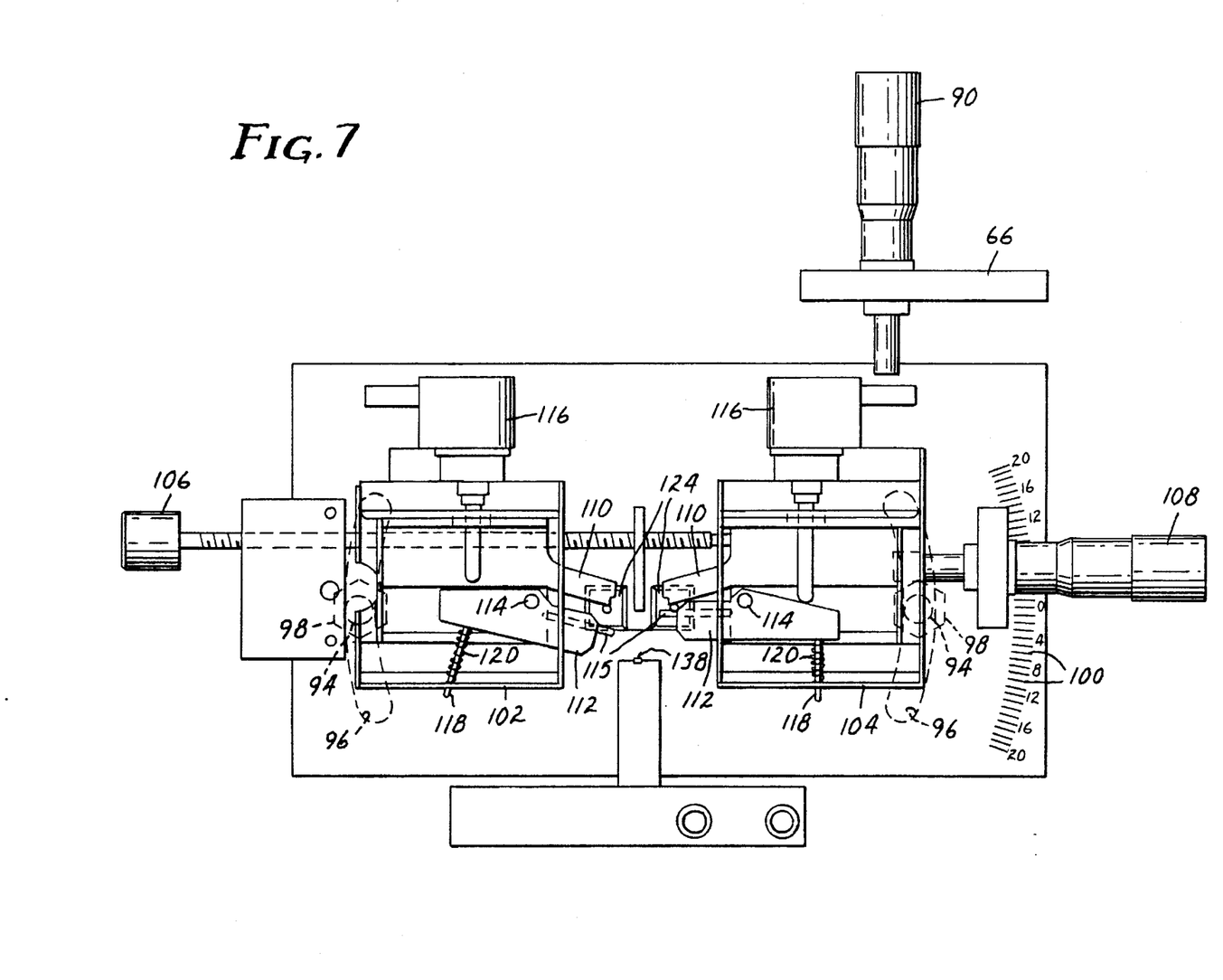
FIG. 7 is an enlarged view of a portion of the apparatus depicted in FIG. 6.

A lower mounting plate 84 is fixed to the subframe 66. An upper surface of the lower mounting plate 84 carries a linear bearing assembly 86 that, in turn, is connected to an upper mounting plate 88. A micrometer adjustment mechanism 90, as shown in FIGS. 6–7, is supported by the subframe 66 and is used to adjust the upper mounting plate 88 for selective, horizontal, front-to-back movement of the upper mounting plate 88 relative to the lower mounting plate 84 when desired.

An angulation plate 92 (not shown in FIG. 7) rests atop the upper mounting plate 88, and is rigidly connected to a pair of threaded vertical rods 94 (FIG. 7) that pass through respective arcuate slots 96 of the upper mounting plate 88. A nut 98 is threaded onto each rod 94, and is connected to a lever (not shown).

The nuts 98 are located beneath the upper mounting plate 88. After the levers are turned to loosen the nuts 98, the angulation plate 92 may be pivoted about a vertical axis relative to the upper mounting plate 88. As shown in FIG. 6, one end of the angulation plate 92 has a notch that is located above a set of indicia marks 100, so that the user can determine the rotative position of the angulation plate 92 relative to the upper mounting plate 88 before tightening the nuts 98 to fix the position of the plate 92.

The angulation plate 92 is shown in the drawings for exemplary purposes as aligned in parallel fashion, or "0" angulation, relative to the upper mounting plate 88. Advantageously, the angulation plate 92 enables the operator to easily adjust the angle, or "angulation", of the attachment relative to the central axis of the band as may be prescribed by the orthodontist.

A band holding fixture comprises a pair of band clamping mechanisms 102, 104 that are movably connected to the angulation plate 92 by metal slides. A band diameter adjustment knob 106 is connected to a threaded rod that passes through a threaded wall of the band clamping mechanism 102. The threaded rod also bears against a wall of the band clamping mechanism 104. Rotation of the knob 106 about a horizontal axis moves the band clamping mechanism 102 in a horizontal direction, either away or toward the band clamping mechanism 104. Spring pressure is applied to the assembly 102 to keep the end of the rod in contact with the mechanism 104.

A micrometer band position adjustment knob 108 is mounted on the angulation plate 92, and is coupled to the band clamping mechanism 104. Adjustment of the knob 108 simultaneously moves both of the band clamping mechanisms 102, 104 in a horizontal direction either away or toward the knob 108 relative to the angulation plate 92.

Each of the band clamping mechanisms 102, 104 includes a stationary stop 110 having a shoulder. The shoulders of the stops 110 receive opposite sides of a band, such as the band 22.

Each band clamping mechanism 102, 104 includes a clamping arm 112 that is movable in an arc about a pivot 114. For illustrative purposes, the clamping arm 112 of the band clamping mechanism 102 is shown in FIG. 7 in an open position to receive a band, while the clamping arm 112 of the band clamping mechanism 104 is shown in a closed position to clamp a band between a horizontal cylindrical pin 115 of the arm 112 and the shoulder of the stop 110. In practice, however, the clamping arms 112 of both mechanisms 102, 104 open and close simultaneously.

A single acting pneumatic piston and cylinder assembly 116 is mounted on each band clamping mechanism 102, 104 and has a piston rod that, when extended, moves the clamping arm 112 from an open position to a closed position. Each piston and cylinder assembly 116 is connected to a source of pressurized air by tubing, and a solenoid operated air valve interposed in the tubing is connected to a foot pedal switch for opening the clamping arms 112 when desired.

A horizontally extending shaft 118 extends forwardly from each clamping arm 112 and through a slot in the front of a housing for each band clamping mechanism 102, 104. A coiled compression spring 120 surrounds each shaft 118, and urges the respective clamping arm 112 toward an open position.

Figure 8:
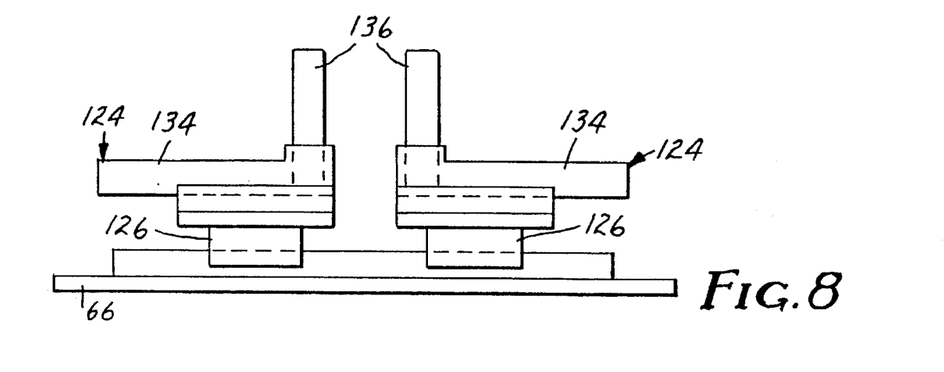
FIG. 8 is an enlarged front elevational view of a lower electrode assembly of the apparatus shown in FIGS. 4–7.
Figure 9:
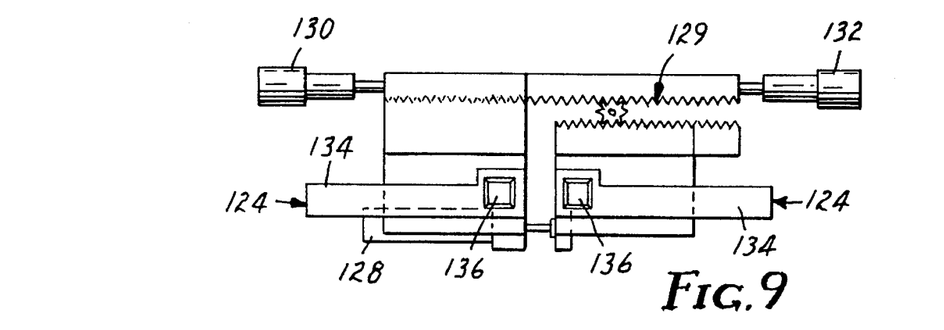
FIG. 9 is a plan view of the lower electrode assembly illustrated in FIG. 8, but shown with two electrode sections of the assembly in an orientation somewhat closer to each other.

A lower electrode assembly 122 is illustrated in FIGS. 5, 8 and 9, and includes two movable, clamping electrode sections 124 that are each mounted on a linear bearing assembly 126 connected to the subframe 66. A conductive strap (not shown) electrically connects the assembly 122 to the power supply 52. A cylinder of a double acting pneumatic piston and cylinder assembly 128 is fixed to one electrode section 124, and a piston rod of the assembly 128 is coupled to the other electrode section 124.

The piston and cylinder assembly 128 moves the lower electrode sections 124 either toward or away from each other as desired. As shown in FIG. 9, a rack and gear mechanism 129 interconnects the electrode sections 124 to assure that both sections 124 move equal distances simultaneously in a horizontal, x-axis direction. The piston and cylinder assembly 128 is connected by tubing to a source of pressurized air, and solenoid operated air valves interposed in the tubing are connected to a second foot pedal switch.

A micrometer stop gauge 130 (FIG. 9) is mounted on the subframe 66 for limiting movement of the electrode sections 124 away from each other by the piston and cylinder assembly 128. A micrometer stop gauge 132 is also mounted on the subframe 66 to limit the distance between the electrode sections 124 when the latter are moved toward each other by the piston and cylinder assembly 128.

Each electrode section 124 includes a horizontal leg 134 and a vertical leg 136 removably received in a channel of the horizontal leg 134. Each vertical leg 136 includes a recess (not shown) at its upper end to receive either the mesial portion or the distal portion of the attachment to be welded to the band. The vertical legs 136 of the electrode sections 124 function as a holder for releasably receiving the attachment. When the electrode sections 124 are moved toward each other, the micrometer stop gauge 132 insures that undue pressure is not exerted on the attachment to deform the latter or cause the latter to snap out of the recesses of the vertical electrode section legs.

Optionally, both of the vertical legs 136 may be removed and replaced with a single vertical member having spaced apart legs for reception in the channels of the horizontal electrode section legs. Such single members are sometimes preferred for use with certain attachments such as buttons, when a movable, clamping-type lower electrode assembly is not desired.

Finally, an air nozzle 138 (FIGS. 5 and 7; not shown in FIG. 6) is connected to the frame 42, and is coupled by tubing to a source of pressurized air. A solenoid air valve is interposed in the tubing leading to the air nozzle 138 and is also electrically connected to the controller 62 for initiating a blast of air toward the welding site directly adjacent the upper electrode 50. The blast of air is sufficient to blow away slag or other debris away from the welding site.

In use, the operator depresses the foot switch (not shown) connected to the cylinder assembly 128 to extend the latter in a direction such that the lower electrode sections 124 are moved away from each other to allow the attachment to be placed onto the electrode legs 136. Next, an orthodontic attachment such as the buccal tube attachment 28 is placed in the recesses of the lower electrode section legs 136 in an orientation wherein the outer, or buccolabial surfaces of the attachment are facing downwardly and in contact with upwardly facing surfaces of the electrode section legs 136. Preferably, the recesses of the electrode section legs 136 are complemental in configuration to the adjacent surfaces of the attachment, so that mating contact between the attachment and the electrode section legs 136 is achieved.

When the foot switch is released, the cylinder 128 retracts and applies pressure through the electrode legs 136 to clamp the attachment. Next, the operator depresses the second foot switch which causes air to be released from cylinders 116 in order to open the arms 112. An orthodontic band such as band 22 is placed in the space between the shoulders of the stops 110 and the pins 115 connected to the arms 112. The operator then releases the second foot switch which causes air to be directed to the piston and cylinder assemblies 116 in order to extend their respective piston rods. As the piston rods extend, the arms 112 simultaneously swing about pivots 114 to cause the band to be clamped between the pins 115 and the stops 110.

The controller 62 and the microstepping drive 77 then begin a program sequence to provide spot welds for the assembly 20 in automated fashion. As one example, the stepmotor 76 may first be actuated to swing the subframe 66 in an arc to a position wherein a mesial flange of the attachment is directly between the upper electrode 50 and the lower electrode assembly legs 136. The controller 62 then activates the welding power supply 52 which directs current between the upper electrode 50 and the lower electrode assembly 122 and resistance weld the inner or lingual surface of the mesial flange of the attachment to the outer or buccolabial surface of the band.

The current may be supplied in each weld position in one or more pulses. Preferably, a first pulse of current at relatively low power is provided to help break surface oxides and prepare the surfaces for welding. A second pulse immediately follows at greater power to provide a strong finish weld.

In practice, the current flows in a direction from the upper electrode 50 to the lower electrode assembly 122, although reverse current flow is also possible. Importantly, the lower electrode assembly 122 has a larger area of surface in contact with the attachment than the area of contact between the upper electrode 50 and the inner surface of the band. As a consequence, a larger deformation, if any, of the metallic surfaces will occur on the inside of the band rather than on the outer surface of the attachment where such deformation would be more visible.

Next, the controller 62 actuates the solenoid valves connected to the piston and cylinder assembly 60 so that the piston rod of the latter retracts and moves the carriage 54 rearwardly relative to the frame 42 until the rear end of the piston rod is in contact with the rear stop 64. At that time, the upper electrode 50 and the lower electrode assembly 122 are directly adjacent another location on the assembly 20 that is adjacent the mesial flange, but spaced in a laterally offset, gingival direction relative to the location of the first spot weld. The controller 62 then activates the weld head 46 and the power supply 52 causes a second weld to be provided between the mesial flange and the band.

Next, the stepmotor 76 is actuated by the microstepping drive 77 to swing the subframe 66 in an arc until the distal welding flange of the attachment is directly between the upper electrode 50 and the lower electrode assembly 122. At that time, the controller 62 again activates the weld head 46 and the power supply 52 causes a third spot weld to be applied.

Next, the controller 62 activates the solenoid air valve connected to the piston and cylinder assembly 60 in order to cause the piston rod of the latter to extend and move the carriage 54 forwardly relative to the frame 42 until the carriage 54 is in contact with the front stop 64. The controller 62 again activates the weld head and the power supply 52 causes a fourth spot weld to be applied at a location on the distal welding flange oriented occlusally from the third spot weld.

Subsequently, the microstepping drive 77 activates the stepmotor 76 to swing the subframe 66 back to a central, preferably horizontal position. The operator then depresses both foot switches, causing the flow of pressurized air to the piston and cylinder assemblies 116 to be interrupted whereupon the clamping arms 112 pivot to an open position by means of the springs 120. Air is also directed to the piston and cylinder assembly 128 to move the lower electrode sections 124 away from each other. The welded attachment and band assembly is then removed from the apparatus 40.

Other welding sequences are also possible. Moreover, the apparatus 40 may be used with flangeless brackets and buccal tubes, as well as with a variety of other orthodontic attachments. In each instance, however, it is preferable that the recess of the lower electrode assembly legs 136 for receiving the attachment is complemental in shape to the configuration of the attachment.

As another alternative, the band and attachment may be received in stationary holders, and the welding electrodes may be mounted on a horizontally movable frame that is also swingable in an arc. The frame is movable in response to a preprogrammed series of instructions to bring the electrodes to the four weld locations described above.

Those skilled in the art can appreciate that many other variations, additions and modifications may be made to the presently preferred embodiments of our invention that are described above in detail. Accordingly, the invention should not be deemed limited to the detailed embodiments described above, but only by a fair scope of the claims that follow along with their equivalents.

We claim:

1. An orthodontic assembly comprising:

a metallic band for encircling a tooth, said band having an inner surface and an outer surface;

a metallic orthodontic attachment connected to said band, said attachment having at least one welding flange with an outer surface; and at least one spot weld between each of said at least one flange and said outer surface of said band, said at least one spot weld interconnecting said attachment and said band with a strength sufficient for orthodontic treatment, said outer surface of each welding flange being characterized by a lack of any spot weld deformation having a volume that is greater than the volume of any deformation of the same spot weld on said inner surface of said band.

2. The assembly of claim 1, wherein said attachment has two welding flanges, and wherein at least two spot welds are located on each of said flanges.

3. The assembly of claim 1, wherein said attachment is a button.

4. The assembly of claim 1, wherein said attachment is a lingual sheath.

5. The assembly of claim 1, wherein said attachment is a hook.

6. The assembly of claim 1, wherein said attachment is an eyelet.

7. The assembly of claim 1, wherein said attachment is a buccal tube.

8. The assembly of claim 1, wherein said attachment is a bracket.

* * * * *